United States Patent [19]

Hsu et al.

[11] Patent Number: 5,200,101
[45] Date of Patent: Apr. 6, 1993

[54] ARYLAMINE/HINDERED PHENOL, ACID ANHYDRIDE AND THIOESTER-DERIVED MULTIFUNCTIONAL ANTIOXIDANT, ANTIWEAR AND RUST INHIBITING ADDITIVES

[75] Inventors: Shin-Ying Hsu, Morrisville, Pa.; Andrew G. Horodysky, Cherry Hill, N.J.; Douglas E. Johnson, Pennington, N.J.; David A. Blain, Mount Laurel, N.J.

[73] Assignee: Mobil Oil Corporation, Fairfax, Va.

[21] Appl. No.: 719,407

[22] Filed: Jun. 24, 1991

[51] Int. Cl.$^5$ ........................................... C10M 135/12
[52] U.S. Cl. ................................... 252/47.5; 252/391; 252/402; 558/251; 558/254
[58] Field of Search ...................... 252/47.5, 391, 402; 558/251, 254

[56] References Cited

U.S. PATENT DOCUMENTS

| | | | |
|---|---|---|---|
| 4,189,388 | 2/1980 | Yaffe et al. | 252/47.5 |
| 4,863,622 | 9/1989 | Chiu | 252/47.5 |
| 4,919,831 | 4/1990 | Howdysky | 252/47.5 |
| 5,037,569 | 8/1991 | Salomon | 252/48.2 |

*Primary Examiner*—Jacqueline Howard
*Attorney, Agent, or Firm*—Alexander J. McKillop; Charles J. Speciale; Howard M. Flournoy

[57] ABSTRACT

Arylamine/hindered phenol, acid anhydride and thioester-derived reaction products, have been found to be effective multifunctional antioxidant, antiwear and rust inhibiting additives for lubricants and fuels.

20 Claims, No Drawings

ARYLAMINE/HINDERED PHENOL, ACID ANHYDRIDE AND THIOESTER-DERIVED MULTIFUNCTIONAL ANTIOXIDANT, ANTIWEAR AND RUST INHIBITING ADDITIVES

BACKGROUND OF THE INVENTION

1. Field of the Invention

This application is directed to arylamine/hindered phenol, acid anhydride and thioester-derived reaction products as multifunctional antioxidant, antiwear and rust-inhibiting additives for lubricants and fuels and to compositions containing same.

2. Description of Related Art

The use of arylamines and hindered phenols for their antioxidant properties when incorporated into oleagenous compositions is well known in the lubricant art. The use of sulfur compounds such as thioesters, sulfurized olefins, sulfurized oils and sulfurized fatty acid esters is well known for their antioxidant properties as well as their antiwear and EP characteristics in a variety of products. It is also known that the antirust and antiwear characteristics can, on occasion, be related to common structural features. Antiwear additives may also be good rust inhibitors if the key functional groups are synergistically united. It is believed that antioxidancy can be enhanced with a synergistic combination of sulfur-containing compounds, hindered phenols and arylamines.

This unique class of compounds clearly demonstrates promising antioxidant, rust-inhibiting and antiwear characteristics in lubricants. The syntheses and application of this family of compounds in lubricant compositions have not been disclosed elsewhere and are, therefore, novel. Similar performance advantages are expected with the use of these compositions in hydrocarbon, oxygenated, or mixed fuel formulations.

BRIEF SUMMARY OF THE INVENTION

This invention more particularly provides arylamine/hindered phenol, acid anhydride and thioester derived multifunctional lubricant and fuel additives and fuel and lubricant compositions comprised thereof.

We have now found that antioxidants with both antiwear and antirust characteristics can be obtained through the derivatization as exemplified by FIGS. 1, 2 and 3. These multifunctional antioxidants proved to be very effective antioxidants, rust inhibitors and antiwear additives for lubricants and polymers. Improved antioxidancy is provided by the synergistic combination of hindered phenols, arylamines and sulfur-containing functional groups incorporated in the molecule. The antiwear and rust-inhibiting properties displayed by these multifunctional antioxidants are believed to be imparted by the surface-active groups synergistically integrated within the compositions. The multifunctional antioxidants have a carboxylate group which may attach itself to a metal surface. Surface attachment may also induce a preferable conformation of the molecule involved to form a complex with the metal surface.

Antistaining, antifatiguing, extreme pressure, high temperature stabilizing, friction reducing, detergent/cleanliness and anticorrosion properties are likely to be found in these novel compositions.

It is, therefore, an object of this invention to provide improved lubricant and fuel compositions, novel multifunctional lubricant and fuel additives and the novel use and process of making the described additives.

DESCRIPTION OF THE PREFERRED EMBODIMENTS

The preparation of multifunctional antioxidants claimed in this invention is described in FIGS. 1, 2, and 3. The use of sulfur-containing compounds glycol dimercaptoacetate, pentaerythritol tetramercaptopropionate, and trimethylolpropane trimercaptopropionate in FIGS. 1, 2 and 3 is only for illustration; other sulfur-containing molecules with multi-reactive sites can also be used. These other sulfur containing molecules could be derivatized exactly the same way, or in a generally similar fashion, as illustrated in FIGS. 1, 2 and 3. The molar ratio of acid anhydride, arylamine, and hindered phenol to the molecule with multi-reactive sites can be varied. The hindered phenols and arylamines used here can be other types of hindered phenols and/or arylamines. Hindered phenols or arylamines can be used alone for derivatization as exemplified by FIG. 1 and 2, or can be mixed together for derivatization as exemplified by FIG. 3. The acid anhydride, however, is essential for the derivatization to provide superior lubricant solubility characteristics to the final products.

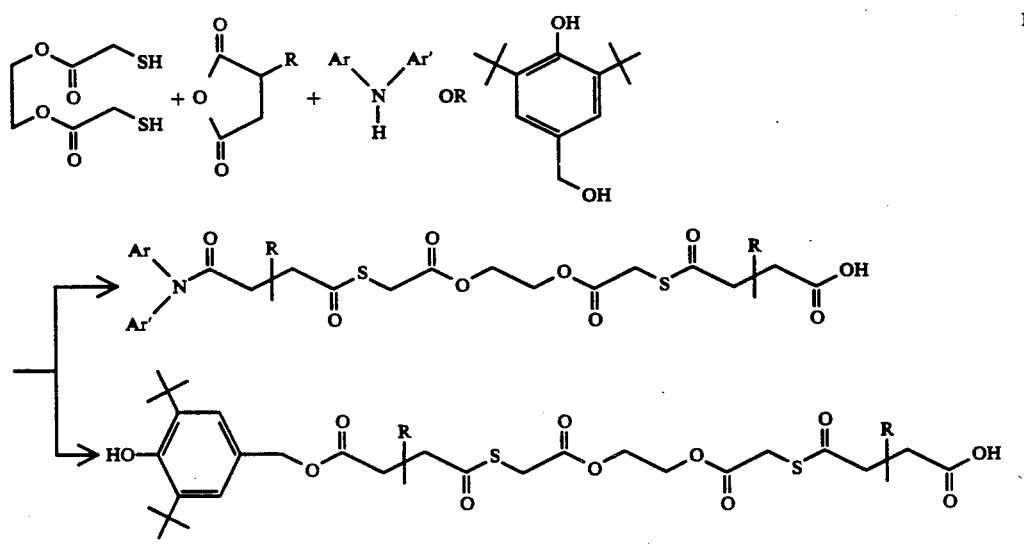

FIG. 1

-continued

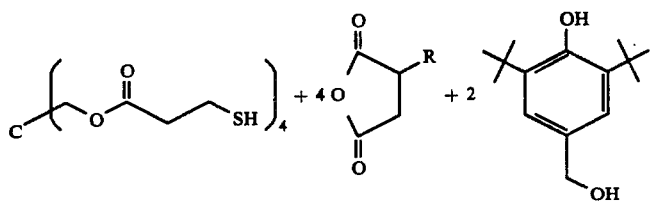

FIG. 2

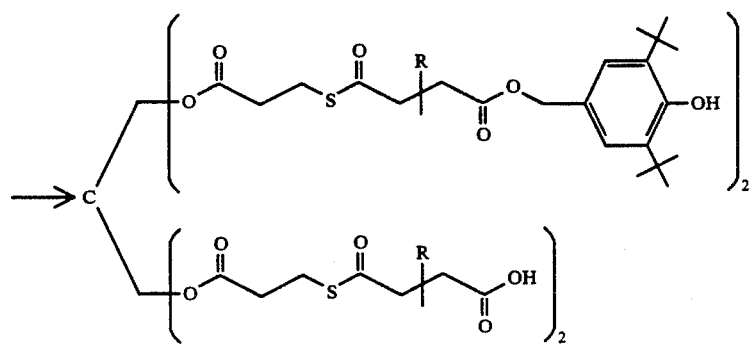

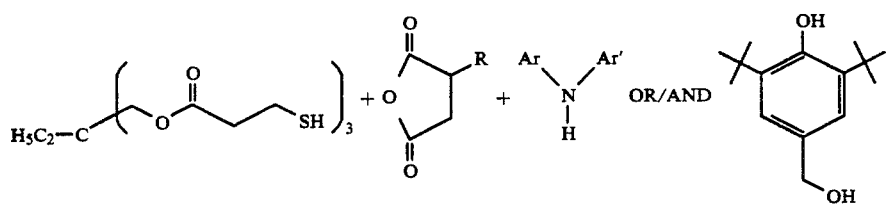

FIG. 3

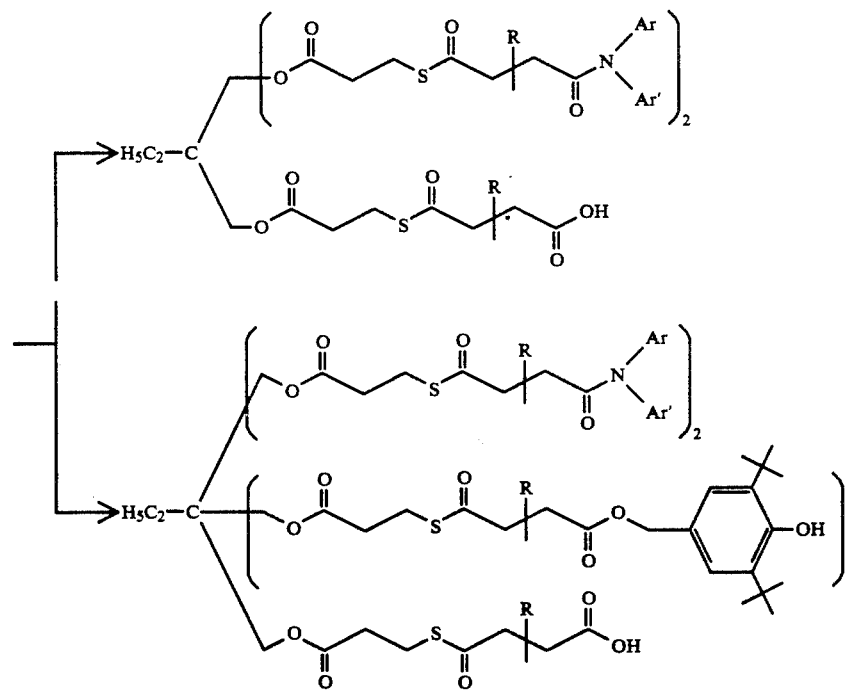

These equations are for illustration only. Other similar reactants can be used. Other products are possible. The illustrations are representative of the structures which could be found in the products. Mixtures are possible, and may, on occasion, be preferable.

R=hydrocarbyl, such as alkyl or alkenyl or a polyhydrocarbyl such as polyisobutenyl, or polypropenyl. Ar and Ar'=substituted aromatics, the substitution for Ar and Ar' can be the same or different. The substitution can be $C_1$ to about $C_{200}$ hydrocarbyl, preferably $C_1$–$C_{18}$, alkyl, alkylaryl, arylalkyl or aryl and can be the same or different and can optionally contain sulfur, nitrogen, and/or oxygen. The position of substitution for Ar and Ar' can be the same or different, preferably at the position para to the position bearing nitrogen.

Suitable sulfur-containing compounds include any appropriate thioester including but not limited to glycol dimercaptoacetate, pentaerythritol tetramercaptopropionate, and trimethylolpropane trimercaptopropionate.

Suitable hindered phenols include but are not limited to 2,6-di-t-alkyl-4-hydroxymethylphenol, 2,6-di-n-alkyl-4-hydroxymethylphenol, 2,6-di-s-alkyl-4-hydroxymethylphenol, 2- or 6-monoalkyl-4-hydroxymethylphenol and 4-hydroxymethylphenol.

Suitable hydrocarbyl acid anhydrides include but are not limited to alkyl or alkenyl succinic anhydrides or similar aliphatic or aromatic dibasic anhydrides such as 2-dodecen-1-yl-succinic anhydride, polyisobutenylsuccinic anhydrides and alkylated phthalic anhydrides.

Suitable arylamines include but are not limited to di(octylphenyl)amine, diphenylamine, monoalkylated diphenylamines and monoalkylated naphthylphenylamines.

Conditions for the above reactions may vary widely depending upon specific reactants, the presence or absence of a solvent and the like. Any suitable set of reaction conditions known to the art may be used. Hydrocarbon solvents such as toluene or xylenes are frequently used. Generally stoichiometric or equimolar ratios of reactants are used. However, more than molar or less than molar amounts may be used. In any event, reaction conditions are not viewed as critical.

Clearly the use of these thioester-derived reaction products provide exceptional antiwear and antioxidant activity with rust-inhibiting properties.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %. It is expected that these materials would also be suitable for use in liquid hydrocarbyl or alcoholic or mixed hydrocarbyl/alcoholic or oxygenated fuel compositions. They are utilized in fuels in amounts of from about 25 to 500 pounds of additive per thousand barrels of fuel and preferably from about 50 to about 250 pounds per 1000 barrels of fuel. Detergent, cleanliness, combustion improving and related fuel improvement properties are expected.

The additives have the ability to improve the above noted characteristics of various oleagenous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may have viscosity indexes ranging from below 50 to above 200 but generally viscosity indexes above 95 may be preferred for some applications. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxyphenyl) ether, phenoxyphenylethers. Ester-based lubricants are highly suitable.

The fuels contemplated as noted hereinabove are liquid hydrocarbon combustion fuels, including oxygenated and alcoholic fuels as well as distillate fuels and fuel oils.

It is to be understood, however, that the compositions contemplated herein can also contain other materials. For example, corrosion inhibitors, extreme pressure agents, low temperature properties modifiers and the like can be used as exemplified respectively by metallic phenates sulfonates, polymeric succinimides, non-metallic or metallic phosphorodithioates and the like. These materials do not detract from the value of the compositions of this invention, rather the materials serve to impart their customary properties to the particular compositions in which they are incorporated.

The following examples are merely illustrative and not meant to be limitations.

EXAMPLE 1

To a solution of glycol dimercaptoacetate (commercial material obtained from Evans Chemical Co.) (21 g, 0.1 mol) in 150 ml toluene was added 2-dodecen-1-yl-succinic anhydride (53.2 g, 0.2 mol). The mixture was refluxed for 4 hours, or until 1.8 ml H$_2$O collected in a Dean-Stark trap. The solvent was evaporated under reduced pressure to afford the product as a yellowish oil (95 g).

EXAMPLE 2

To a solution of glycol dimercaptoacetate (commercial material obtained from Evans Chemical Co.) (21 g.

0.1 mol) in 150 ml toluene was added 2-dodecen-1-yl-succinic anhydride (53.2 g, 0.2 mol) and di(octylphenyl-)amine (commercial material obtained as Vanlube 81 from Vanderbilt Chemical Co.) (39.3 g, 0.1 mol). The mixture was refluxed for 4 hours, or until 1.8 ml $H_2O$ collected in a Dean-Stark trap. The solvent was evaporated under reduced pressure to afford the product as a yellowish oil (108 g).

EXAMPLE 3

To a solution of pentaerythritol tetramercaptopropionate (commercial material obtained from Evans Chemical Co.) (24.4 g, 0.05 mol) in 150 ml toluene was added 2-dodecen-1-yl-succinic anhydride (53.2 g, 0.2 mol) and 2,6-di-t-butyl-4-hydroxymethylphenol (commercial material obtained as Ethanox 754 from Ethyl Corp.) (23.6 g, 0.1 mol). The mixture was refluxed for 4 hours, or until 1.8 ml $H_2O$ collected in a Dean-Stark trap. The solvent was evaporated under reduced pressure to afford the product as a yellowish oil (97 g).

EXAMPLE 4

To a solution of trimethylolpropane trimercaptopropionate (19.3 g, 0.05 mol) in 150 ml toluene was added 2-dodecen-1-yl-succinic anhydride (40 g, 0.15 mol) and di(octylphenyl)amine (commercial material obtained as Vanlube 81 from Vanderbilt Chemical Co.) (39.3 g, 0.1 mol). The mixture was refluxed for 5 hours, or until 1.8 ml $H_2O$ collected in a Dean-Stark trap. The solvent was evaporated under reduced pressure to afford the product as a yellowish oil (93 g).

EXAMPLE 5

To a solution of trimethylolpropane trimercaptopropionate (19.3 g, 0.05 mol) in 150 ml toluene was added 2-dodecen-1-ylsuccinic anhydride (40 g. 0.15 mol), 2,6-di-t-butyl-4-hydroxymethylphenol (commercial material obtained as Ethanox 754 from Ethyl Corp.) (11.8 g, 0.05 mol). The mixture was refluxed for 2 hours, or until 0.9 ml $H_2O$ collected in a Dean-Stark trap, cooled to 25° C., and di(octylphenyl)amine (commercial material obtained from Vanderbilt Chemical Co. as Vanlube 81) (19.7 g, 0.05 mol) was added. The mixture was refluxed for 4 hours, or until about 0.9 ml $H_2O$ collected in the trap. The solvent was evaporated to afford the product as a yellowish oil (85 g).

EVALUATION OF PRODUCTS

The multifunctional antioxidants thus obtained were blended into mineral oils and evaluated for antioxidant performance by the Catalytic Oxidation Test (325° F. for 40 hours, Table 1), and antiwear characteristics by the Four-Ball Wear Test (60 kg load/2000 rpm/200° F. for 30 min, Table 2). The oxidation-inhibiting characteristics of other traditional, commercial arylamine antioxidants in the same mineral oil are also included in Table 1.

CATALYTIC OXIDATION TEST

Basically, in the catalytic oxidation test, the lubricant is subjected to a stream of air which is bubbled through at the rate of five liters per hour at elevated temperatures for a specified time (Table 1, 325° F. for 40 hours). Present in the composition are samples of metals commonly used in engine construction, namely, iron, copper, aluminum, and lead. See U.S. Pat. No. 3,682,980, incorporated herein by reference.

TABLE 1

| Item | Catalytic Oxidation Test (325° F., 40 hrs) | | |
|---|---|---|---|
| | Additive Concentration (wt %) | Change in Acid Number Δ TAN | % Change in Viscosity, Δ KV (%) |
| Base oil (200 second, solvent refined, paraffinic neutral mineral oil) | None | 11.97 | 210 |
| Commercial Arylamine Antioxidant (Ciba-Geigy Irganox L-57) in above oil | 1.0 | 6.42 | 80.5 |
| Example 1 in above oil | 1.0 | 3.10 | 74.5 |
| Example 4 in above oil | 1.0 | 1.30 | 52.3 |
| Example 5 in above oil | 1.0 | 4.23 | 63.0 |

This data demonstrates the improved control of oxidation-induced viscosity and acidity increases.

In the Four-Ball Wear Test, three stationary balls are placed in the lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes. K (as reported in Table 2) the wear coefficient is calculated from the wear volume, V, of the stationary ball. The wear volume is calculated from the wear scar diameter D in mm as follows:

$V = [15.5 D^3 - 0.001033L]D \times 10^3 mm^3$, where L is the machine load in kg. This equation considers the elastic deformation of the steel balls.

WEAR COEFFICIENT $K$

Dimensionless $K$ is defined as $K = \frac{VH}{dN}$ where $V$ = wear volume, $mm^3$ $H$ = hardness 9725 $kg/mm^2$ for 52100 steel $d$ = (23.3 mm/rev) (RPH × Time)

$N$ = (0.408) (Load in kg)

TABLE 2

| Item | Four-Ball Wear Test 60 kg/2000 rpm/30 min/200° F. | | |
|---|---|---|---|
| | Additive Concentration | Wear Scar (mm) | K factor × $10^8$ |
| Base Oil (80% solvent paraffinic bright, and 20% solvent paraffinic neutral lubricant oils) | None | 3.32 | 3960 |
| Example 3 in above oil | 1.0 | 2.28 | 888 |
| Example 4 in above oil | 1.0 | 0.76 | 9.6 |
| Example 5 in above oil | 1.0 | 0.85 | 16.0 |

This data demonstrates the antiwear properties of the multifunctional antioxidants.

The multifunctional antioxidants were blended into a fully formulated industrial oil without a rust inhibitor in a hydroprocessed mineral oil base stock. The multifunctional antioxidants exhibited excellent room- and low-temperature solubility. No haze or precipitate developed on standing for 2 months at room temperature or after 7 days at 4° C. The rust inhibiting and demulsibility properties of the industrial oils with or without the multifunctional antioxidant were determined according to ASTM D665, the Bethlehem Steel Rust Test, and ASTM D1401. Results are shown in Table 3.

TABLE 3

| Test | Fully Formulated Industrial Oil + 0.2% Example 4 | Fully Formulated Industrial Oil Without Rust Inhibitor |
|---|---|---|
| ASTM D665 | | |
| 24 hr, 5% synthetic sea water | Pass moderate/5% rust | severe/100% rust |
| 48 hr, 5% synthetic sea water | | |
| Bethlehem Steel Rust Test | | |
| Part A | Pass | Pass |
| Part B | Pass | Pass |
| Part C | Pass | severe/55% rust |
| ASTM D1401 | | |
| Time to 37 ml water | 5 min | 10 min |
| Time to 3 ml emulsion | 5 min | 10 min |
| Time to break | 5 min | 10 min |

These results demonstrate the excellent rust inhibiting properties of the multifunctional antioxidants. These materials also have an unexpected beneficial effect on demulsibility.

It is clear from Table 1 that the novel multifunctional antioxidants display better antioxidancy than commercial arylamines (Irganox L-57). In addition, these compounds also provide excellent antiwear and rust-inhibiting properties as evidenced by the data in Tables 2 and 3. From these data, it can be concluded that these new additives prepared according to FIGS. 1, 2 and 3 can be good antioxidants, rust inhibitors, and antiwear additives with broad applications in lubricants and fuels.

The multifunctional antioxidants based on hindered phenols and arylamines as described in this patent application are an entirely new family of compounds which exhibit good antioxidant, antirust, and antiwear properties under severe service conditions. These properties can enhance the thermal and oxidative stability of premium quality automotive and industrial lubricants to extend their service life.

We claim:

1. An improved lubricant composition comprising a major proportion of an oil of lubricating viscosity or grease prepared therefrom and a minor multifunctional antiwear, antioxidant, rust inhibiting additive product of reaction prepared by reacting an arylamine with a hydrocarbyl acid anhydride and a thioester in equimolar, less than molar or more than molar amounts at temperatures varying from ambient to about 250° C. under pressures varying from ambient to slightly higher or autogenous for a time sufficient to obtain the desired additive product of reaction.

2. The composition of claim 1 wherein the product has the below generalized structure or mixtures thereof

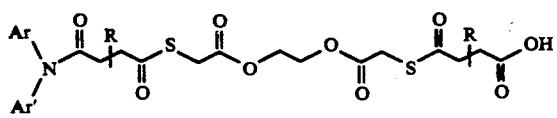

and wherein R is $C_1$ to about $C_{200}$ hydrocarbyl or polyhydrocarbyl, Ar and Ar' are the same or different substituted aromatics having from 6 to about 200 carbon atoms and optionally containing sulfur, nitrogen and or oxygen or mixtures thereof and hydrocarbyl as is selected from alkyl, alkenyl, alkylaryl, arylalkyl or aryl.

3. The composition of claim 1 wherein the product has the following structural formula

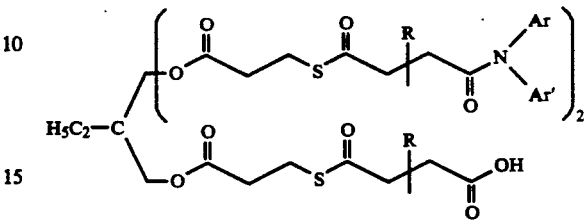

and wherein R is $C_1$ to about $C_{200}$ hydrocarbyl or polyhydrocarbyl, Ar and Ar' are the same or different substituted aromatics having from 6 to about 200 carbon atoms and optionally containing sulfur, nitrogen and or oxygen or mixtures thereof and hydrocarbyl is selected from the group consisting of alkyl, alkenyl, alkylaryl, arylalkyl or aryl.

4. The composition of claim 1 wherein the reactants are glycol dimercaptoacetate, 2-dodecen-1-ylsuccinic anhydride and di(octylphenyl)amine.

5. The composition of claim 1 wherein the reactants are trimethylolpropane trimercaptopropionate, 2-dodecen-1-ylsuccinic anhydride and di(octylphenyl)amine.

6. A lubricant composition in accordance with claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1), (2) or (3).

7. The composition of claim 6 wherein the lubricant contains from about 0.001 to about 10 wt % based on the total weight of the composition of the additive product of reaction.

8. The composition of claim 6 wherein the lubricant is a synthetic oil.

9. The composition of claim 6 wherein the lubricant is a mineral oil.

10. A process of preparing a multifunctional antioxidant, antiwear, rust inhibiting additive product by reacting an aryl amine with a hydrocarbyl acid anhydride and a thioester in equimolar, less than molar or more than molar ratios at temperatures varying from ambient to about 250° C. under pressures varying from ambient to slightly higher or autogenous for a time sufficient to obtain the desired additive product of reaction.

11. The process of claim 10 wherein the product has the following structural formula

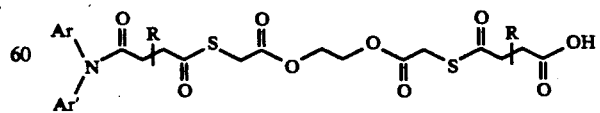

and wherein R is $C_1$ to about $C_{200}$ hydrocarbyl or polyhydrocarbyl, Ar and Ar' are the same or different substituted aromatics having from 6 to about 200 carbon atoms and optionally containing sulfur, nitrogen and or oxygen or mixtures thereof and hydrocarbyl is selected from the group consisting of alkyl, alkenyl, alkylaryl, arylalkyl or aryl.

12. The process of claim 10 wherein the product has the following structural formula

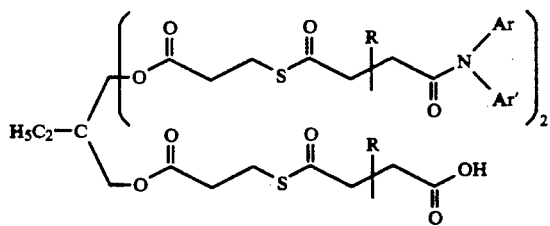

and wherein R is $C_1$ to about $C_{200}$ hydrocarbyl or polyhydrocarbyl, Ar and Ar' are the same or different substituted aromatics having from 6 to about 200 carbon atoms and optionally containing sulfur, nitrogen, and or oxygen or mixtures thereof and hydrocarbyl is selected from the group consisting of alkyl, alkenyl, alkylaryl, arylalkyl or aryl.

13. The process of claim 10 wherein the reactants are glycol dimercaptoacetate, 2-dodecen-1-ylsuccinic anhydride and di(octylphenyl)amine.

14. The process of claim 10 wherein the reactants are trimethylolpropane trimercaptopropionate, 2-dodecen-1-ylsuccinic anhydride and di(octylphenyl)amine.

15. A product of reaction prepared by reacting an aryl amine with a hydrocarbyl acid anhydride and a thioester in equimolar, less than molar or more than molar amounts at temperatures varying from ambient to about 250° C. under pressures varying from ambient to slightly higher or autogenous for a time sufficient to obtain the desired additive product of reaction.

16. The product of reaction of claim 15 wherein the product has the following formula:

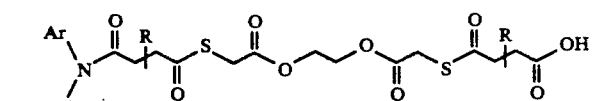

and wherein R is $C_1$ to about $C_{200}$ hydrocarbyl or polyhydrocarbyl, Ar and Ar' are the same or different substituted aromatics having from 6 to about 200 carbon atoms and optionally containing sulfur, nitrogen and or oxygen and hydrocarbyl is selected from the group consisting of alkyl, alkenyl, alkylaryl or arylalkyl or aryl.

17. The product of claim 16 wherein the reactants are glycol dimercaptoacetate, 2-dodecen-1-ylsuccinic anhydride and di(octylphenyl)amine.

18. The product of claim 16 wherein the reactants are trimethylolpropane trimercaptopropionate, 2-dodecen-1-ylsuccinic anhydride and di(octylphenyl)amine.

19. A method of preparing an improved lubricant composition comprising adding to said lubricant a minor multifunctional antioxidant, antiwear, rust inhibiting amount of an additive product of reaction as described in claim 15.

20. The method of claim 19 wherein said minor amount is from about 0.001 to about 10 wt % based on the total weight of the composition of said additive product of reaction.

* * * * *